United States Patent [19]

Ngo

[11] Patent Number: 4,467,803
[45] Date of Patent: Aug. 28, 1984

[54] ORAL TEMPORARY TOTAL HEMOSTATIC CLAMPS

[76] Inventor: Tuyen N. Ngo, 495 E. Williams St., #5, San Jose, Calif. 95112

[21] Appl. No.: 364,215

[22] Filed: Apr. 1, 1982

[51] Int. Cl.³ ............................................ A61B 17/12
[52] U.S. Cl. .................................... 128/325; 128/346
[58] Field of Search ..................... 128/303 R, 321–326, 128/346, 12–17

[56] References Cited

U.S. PATENT DOCUMENTS

| | | | |
|---|---|---|---|
| 480,165 | 8/1892 | Bates | 128/346 |
| 1,437,995 | 12/1922 | Richter | 128/17 |
| 1,727,879 | 9/1929 | Hodlick et al. | 128/17 |
| 1,913,770 | 6/1933 | Olenik | 128/321 |
| 2,100,730 | 11/1937 | Black | 128/346 |
| 2,250,605 | 7/1941 | Rubin | 128/346 |
| 3,270,745 | 9/1966 | Wood | 128/325 |
| 3,326,216 | 6/1967 | Wood | 128/325 |
| 3,439,522 | 4/1969 | Wood | 72/410 |
| 3,631,707 | 1/1972 | Miller | 72/410 |
| 3,732,719 | 5/1973 | Pallota | 72/410 |
| 3,775,826 | 7/1972 | Reed | 29/212 D |
| 3,779,248 | 12/1973 | Karman | 128/321 |
| 3,809,094 | 5/1974 | Cook | 128/321 |
| 3,827,277 | 6/1973 | Weston | 72/410 |
| 3,867,944 | 2/1975 | Samuel | 128/325 |
| 4,073,179 | 2/1978 | Hickey | 72/409 |
| 4,187,712 | 4/1977 | Samuels | 72/410 |
| 4,242,902 | 10/1977 | Green | 72/410 |

OTHER PUBLICATIONS

Brief Communications, *Annals of Surgery*, 1933, pp. 794–796.

*Primary Examiner*—Dalton L. Truluck

[57] ABSTRACT

This invention is directed to hemostasis in the lips and the mucosal side of the cheek. These devices are not used for stopping each vessel from bleeding but are used for temporarily stopping the total blood supply to the entire surgical area. Model A has a pair of lip-shaped jaws for providing hemostasis in the entire upper or lower lip. The jaws are curved to conform to the entire lip and formed to interlock to permit longitudinal movement in jaw menbers. This structure is used for changing the size of jaws to adapt to different sizes of lips. Model A has two pairs of arms for maintaining a constant hemostatic pressure throughout the entire lip. Another design is constructed to provide hemostasis in a small area on the lip. Its jaws are semicircular and curved 90° with semicircular parts of arms so that the surgeon can have access to surgical field easily without obstruction. Another model is designed to obtain hemostasis in the mucosal side of the cheek. Its circular jaws are combined with a pair of 90° angulated arms. In the second and third models, the jaw-arm 90° angulation is combined with an interlocked longitudinally movable system for keeping a constant parallel between the jaws in order to obtain hemostasis most effectively. A locking bolt-like bar has two threads. The distal thread is used for keeping the nut on the bar when releasing the device. The proximal thread is used for desirably adjusting the hemostatic pressure.

1 Claim, 14 Drawing Figures

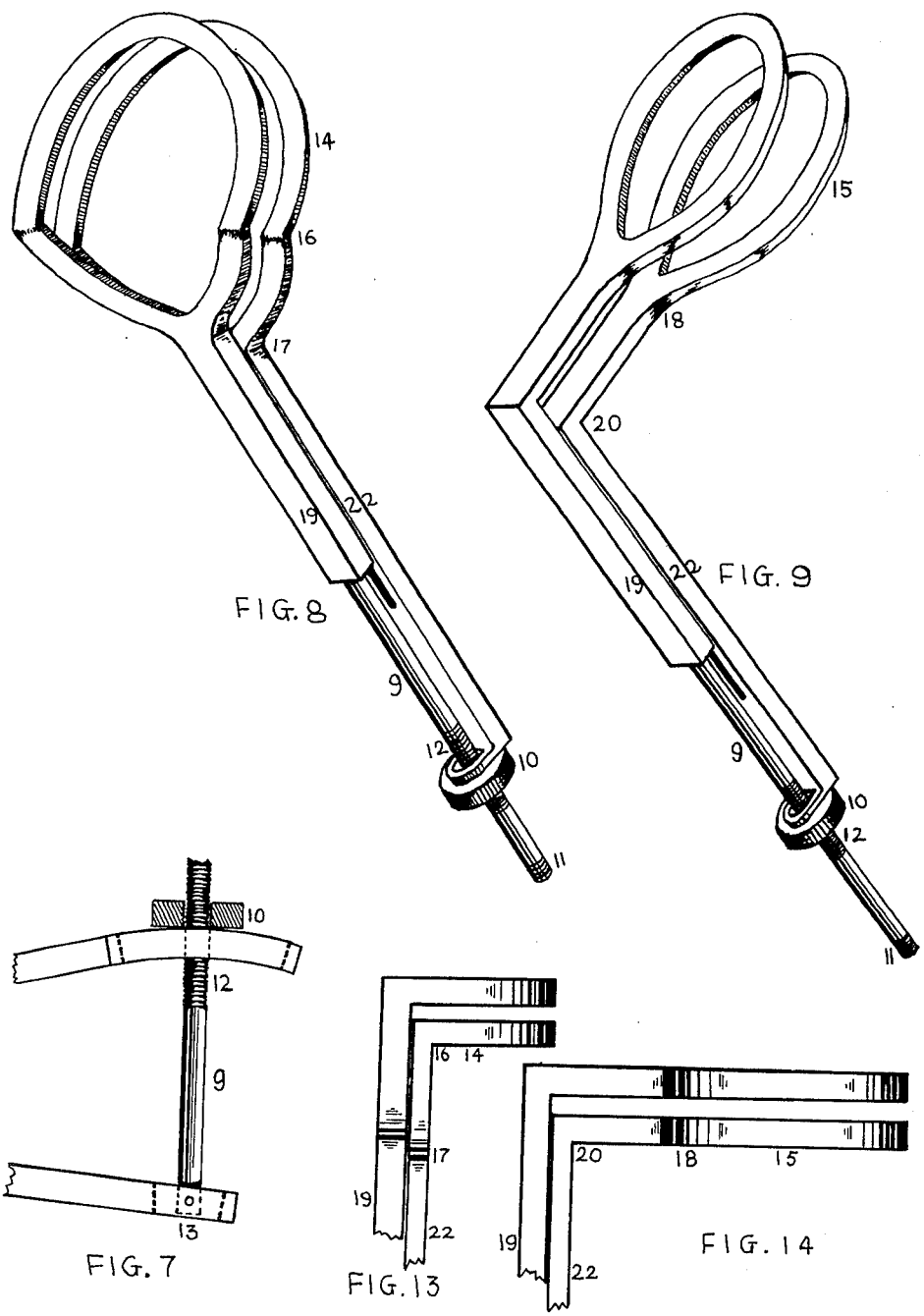

ORAL TEMPORARY TOTAL HEMOSTATIC CLAMPS

BACKGROUND OF THE INVENTION (1) Field of Invention

This invention relates to surgical instruments for oral surgery. The procedure is based on temporarily stopping the total blood supply to the entire surgical area in the lip and the mucosal side of the cheek. These devices are not used for stopping each individual vessel from bleeding but are used for stopping the total blood supply to the entire surgical area.

(2) Description of the Prior Art

Instruments of the general type are known in the art and are exemplified by the following patents and publication:

In the patent to Hoddick et Al U.S. Pat. No. 1,727,879 and Richter U.S. Pat. No. 1,437,995 both showed oral instruments conforming to mouth morphology but in actuality conforming to the maxillary bone for facilitating deep oral surgery. The primary advantage of my device has jaws which conform to the whole upper or lower lip whose purpose is to provide hemostatic pressure to the entire lip.

In the patent to Olenik U.S. Pat. No. 1,913,770 noted ring jaws used for holding an absorbent pad and sponge for stanching the flow of blood from a wound left by the removal of one tonsil in such manner as to prevent no interference to an immediately succeeding operation on the opposite tonsil. My instrument provides hemostasis to the entire surgical area prior to and during surgery not after incision and/or excision of oral tissue.

An inter-ringed clamp of Wolfson in the Annals of Surgery, 1933, pp. 794–796, is a clamp which has unequal rings; and used to hold and secure tissues and viscera in abdominal operation or vaginal operation; but is not used for hemostatic purposes.

In the patent to Bates U.S. Pat. No. 480,165 had a circular ring of jaw members which are of the same morphology as in my Model C; but is used on the skin for taking up the skin immediately around a snake-bite or other affection and cutting off the blood flow to and from the wound or affection whereby the poison or disease will be prevented from disseminating through the vascular system of the patient. Moreover, Bate's device has different types of arms compared with mine.

In the patent to Rubin U.S. Pat. No. 2,250,605 also had circular ring members but they are of unequal size and used as a tissue holder and not for hemostatic purposes. Rubin's device has different types of arms compared with mine.

In the patent to Black U.S. Pat. No. 2,100,730 has sliding hugging jaws for adjustability but has a different structure compared with my device. Moreover, Black's clamp is used for holding animals firmly and securely during the time that the animals are being operated upon or treated for any purposes.

SUMMARY OF THE INVENTION

Surgery of the lips and the mucosal sides of the cheek causes profuse bleeding. One objective of my invention is to prevent profuse bleeding of the entire surgical area by temporarily stopping the blood flow in the entire surgical field. These devices are not used for stopping each blood vessel from bleeding but are used for temporarily stopping the total blood supply to the entire surgical field. In order to stop the total blood flow in surgical field, the jaws of my invention are confined to the entire surgical area; one jaw being in the mouth and the other jaw is outside of the mouth.

These devices have the locking bar system which has a bolt-like bar with spiral groove-like segments so that we can release these devices gradually in order to easily find out which vessels are still bleeding and then use regular hemostatic clamps to easily stop each vessel from bleeding.

Another advantage of my devices (in Model B and C) is to combine the sliding hugging system in arms with the 90° jaw-arm angulation so that two opposed jaws are always parallel in order to stop bleeding most effectively.

The other objective of my invention is to provide a sufficient clear surgical field by having little or no bleeding during the procedure so that surgeons can operate easily, rapidly and precisely.

Another advantage of my invention (in Model A) is to have two pairs of jaws for maintaining constant hemostatic pressure throughout the entire surgical lip.

Another advantage of my invention (in Model A) is to have the sliding hugging system in jaws for changing the size of the jaw members in order to adapt to different sizes of entire upper or lower lips. My sliding hugging system is simpler than that of Black's device in that the jaws are thinner and thus easily inserted in the mouth.

BRIEF DESCRIPTION OF THE DRAWINGS

FIG. 7 is a side elevation of locking-bar system of Model A.

FIG. 8 is a perspective view of Model B.

FIG. 9 is a perspective view of Model C.

FIG. 13 is a side elevation of Model B.

FIG. 14 is a side elevation of Model C.

DESCRIPTION OF THE PREFERRED EMBODIMENT

Figure 1:
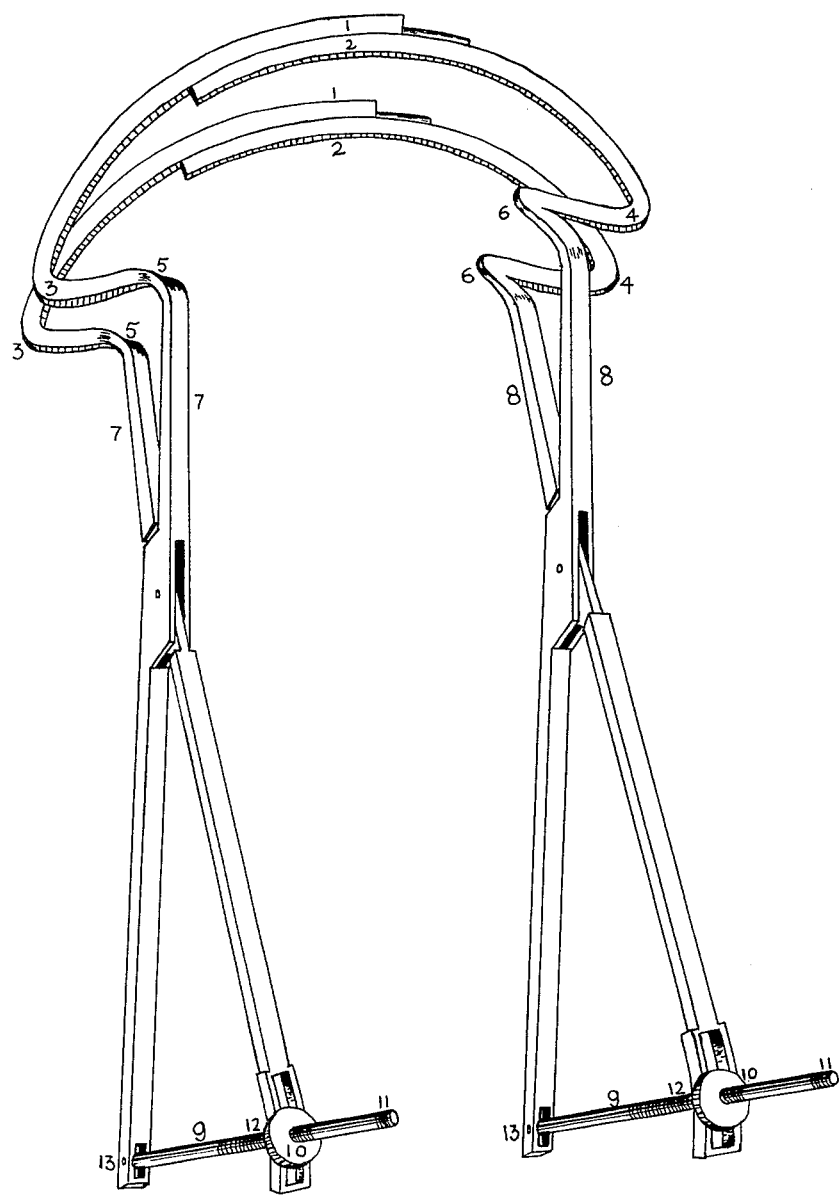
FIG. 1 is a perspective view of Model A.
Figure 2:
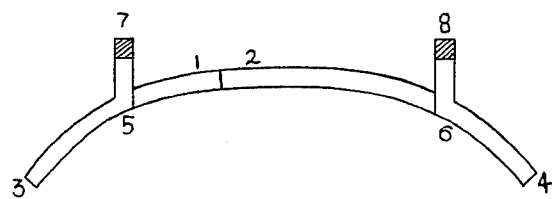
FIG. 2 is an upward-side elevation of one jaw of Model A.
Figure 5:
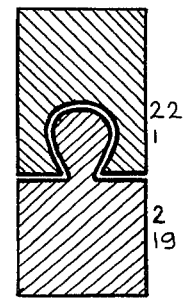
FIG. 5 is an enlarged sectional view of sliding hugging system.
Figure 3:
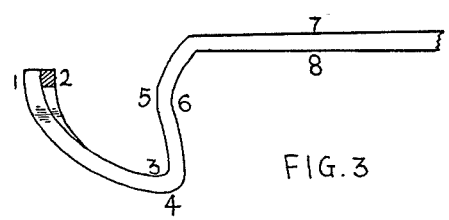
FIG. 3 is a left-lateral-side elevation of one jaw of Model A.
Figure 6:
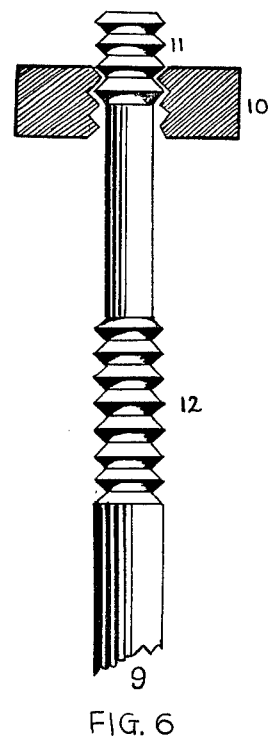
FIG. 6 is a perspective view of locking-bar system.
Figure 4:
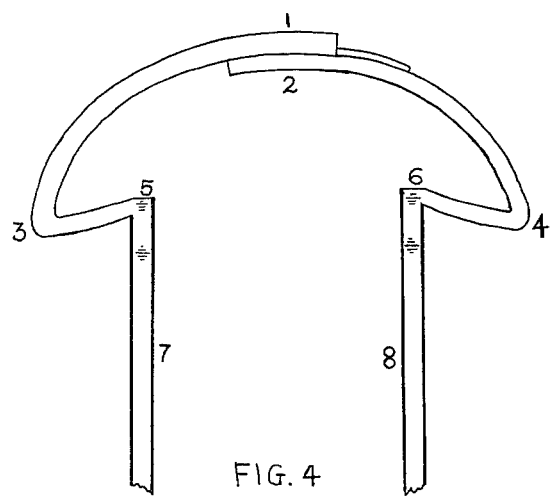
FIG. 4 is a front elevational view of one jaw of Model A.
Figure 10:
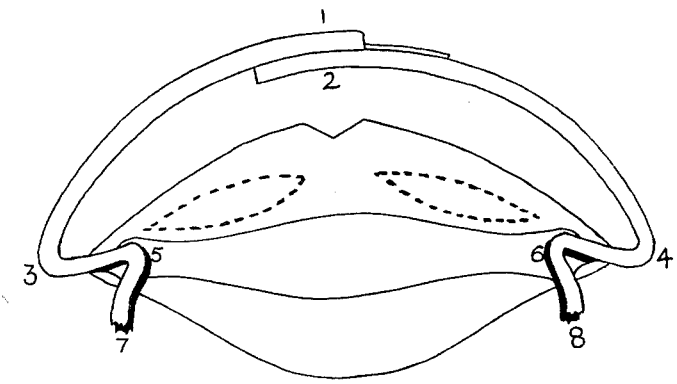
FIG. 10 is a front elevation of lip operation with using Model A.

Model A, shown in FIG. 1, comprises a pair of opposed jaws which are curved to conform to the entire upper or lower lip, shown in FIG. 10, so that we can perform a plastic surgery so that during plastic surgery, it is possible to adjust the size and/or shape of the entire upper and/or lower lip and we can perform other type of surgery on the entire upper or lower lip. Each jaw includes 2 parts 1,2, shown in FIGS. 2,3,4, which are connected by the sliding hugging system. The sliding hugging system comprises the curved channel in the left part of each jaw and a curved rod-like segment on the right part of each jaw as shown in FIG. 1. An enlarged sectional view of this sliding hugging system is shown in FIG. 5. The sliding hugging system is used for changing the size of jaws in order to adapt to different size of the entire upper or lower lip. Model A has two pairs of arms. Each pair has a locking bar system as shown in FIG. 6. This system comprises bolt-like bar 9 that can pivot at the end of the lower arm 13 and is locked at the end of the upper arm by a nut 10. The bolt-like bar has two spiral groove-like segments 11,12. The distal segment 11 keeps the nut when releasing this device. The proximal segment 12 is used for changing the distance between opposed jaws in order to adjust a desirable hemostatic pressure so that after incising and/or excising lip tissues, we can release the device gradually in order to easily find out which vessels are still bleeding and then use regular hemostatic clamps to easily stop each vessel from bleeding.

Figure 11:
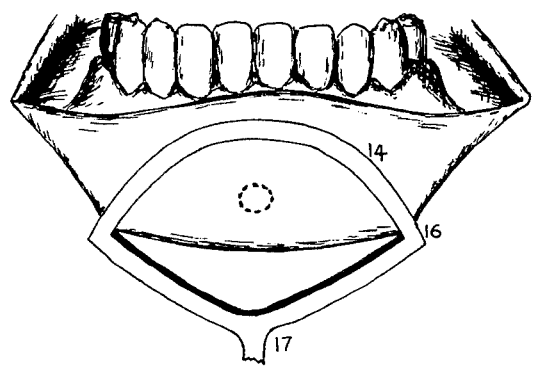
FIG. 11 is a perspective view of lip operation with using Model B.

Model B, shown in FIG. 8, comprises a pair of semicircular jaws 14 which are curved 90° with a pair of semicircular parts of the arms so that the surgeon can have access to the surgical field easily without obstacle which may be caused by the arms of the device. This device is used for lip surgery which need operation only in a small area as shown in FIG. 11. For example: Biopsy, Polype, ect. The arm 19,22 of Model B has the sliding hugging system which comprises a channel in the lower arm 22 and a rod-like segment on the upper arm 19. An enlarged sectional view of this system is the same structure as in Model A which is shown in FIG. 5. The end of arms is the locking bar system as shown in FIG. 6. This system comprises a bolt-like bar 9 which is elongated from the upper arm 19 and locked at the end of the lower arm by a nut 10. The bolt-like bar 9 has two spiral groove-like segments 11,12 like that of Model A. The combination of the sliding hugging system and arm-jaw 90° angulation 16 as shown in FIG. 13 is used for keeping constantly parallel between two opposed jaws so that we can maintain the constant pressure throughout the entire surgical area.

Figure 12:
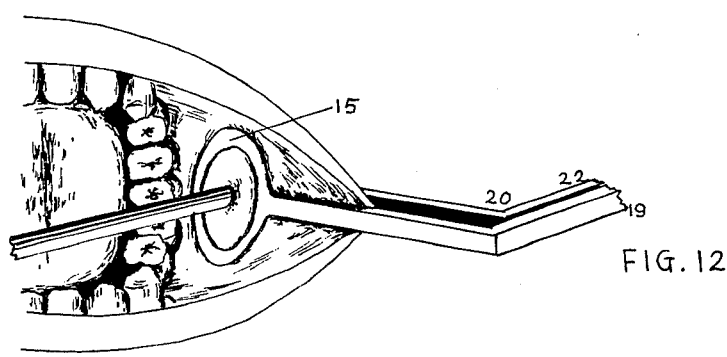
FIG. 12 is a perspective view of deep oral operation with using Model C.

Model C, shown in FIG. 9, comprises a pair of equal circular jaws 15 which are connected with segment 18-20 of the arms so that we can use to operate a deep oral surgery on the mucosal side of the cheek. For example: Facial dimple making as shown in FIG. 12, biopsy, tumor excision, ect. Model C has a pair of 90° angulated arms as shown in FIG. 14. At the end of arms is the locking bar system which is the same one of Model B. The combination of the sliding hugging system and the 90° angulated arm is used for keeping a constantly parallel between two opposed jaws with the same purpose of Model B.

I claim:

1. A surgical instrument for hemostasis of the entire upper or lower lip comprising:

a pair of integral transversely elongated lip-shaped jaw members, said jaw members having right and left parts and being curved to conform to the whole upper or lower lip adapted to totally stop blood flow in the entire surgical field when closed together, said jaw members including thereon an interlocked longitudinally movable adjustable means for changing the size of the jaws to adapt to different lip sizes, said adjustable means comprising a curved channel means in one of said jaw parts and a curved rod-like segment in the other part of said jaws, said rod segment being slidably received in said curved channel means;

two pairs of arms for maintaining constant hemostatic pressure throughout the entire upper or lower lip, each pair of arms connected to said jaw members at one end and comprising upper and lower arm pairs, each pair being pivotally connected intermediate the ends, said arm pairs also including at the opposite ends thereof an adjustable pressure regulating means comprising a bolt like locking bar pivotally connected on one of said pair arms and a bar receiving slot and nut means on the other of said pair arms which receives said bar, said bolt like bar having two separated thread segments, the distal thread segment being used for keeping the nut means on the bar when releasing the instrument, the proximal thread segment being used to release the pressure gradually in order to easily identify which vessels are still bleeding so that a surgeon can easily stop each vessel from bleeding by regular hemostatic clamps.

* * * * *